United States Patent
Lin et al.

(10) Patent No.: US 9,972,406 B2
(45) Date of Patent: May 15, 2018

(54) MODELING METHOD FOR ORTHOPEDIC CASTS

(71) Applicant: The Chinese University of Hong Kong, Hong Kong (CN)

(72) Inventors: Hui Lin, Hong Kong (CN); Defeng Wang, Hong Kong (CN); Lin Shi, Hong Kong (CN)

(73) Assignee: THE CHINESE UNIVERSITY OF HONG KONG, Hong Kong (CN)

( * ) Notice: Subject to any disclaimer, the term of this patent is extended or adjusted under 35 U.S.C. 154(b) by 216 days.

(21) Appl. No.: 15/065,658

(22) Filed: Mar. 9, 2016

(65) Prior Publication Data

US 2017/0262611 A1    Sep. 14, 2017

(51) Int. Cl.
| | |
|---|---|
| G06F 19/00 | (2018.01) |
| A61F 5/01 | (2006.01) |
| G05B 19/4099 | (2006.01) |
| A61F 5/058 | (2006.01) |

(52) U.S. Cl.
CPC .............. *G16H 50/50* (2018.01); *A61F 5/013* (2013.01); *A61F 5/05841* (2013.01); *G05B 19/4099* (2013.01); *G06F 19/3437* (2013.01); *G05B 2219/49023* (2013.01)

(58) Field of Classification Search
CPC .. G06F 19/3437; A61F 5/05841; A61F 5/013; G05B 19/4099; G05B 2219/49023
See application file for complete search history.

(56) References Cited

U.S. PATENT DOCUMENTS

| | | | | |
|---|---|---|---|---|
| 4,854,310 A | * | 8/1989 | Lee ...................... | A61F 5/05866 602/21 |
| 5,824,085 A | * | 10/1998 | Sahay ................. | A61F 2/30942 128/898 |
| 6,613,006 B1 | * | 9/2003 | Asherman ............... | A61F 13/04 602/20 |
| 8,771,365 B2 | * | 7/2014 | Bojarski ............. | A61F 2/30942 606/86 R |
| 2007/0015995 A1 | * | 1/2007 | Lang ...................... | A61B 5/055 600/407 |
| 2008/0183115 A1 | * | 7/2008 | Pierce ................... | A61F 13/041 602/13 |
| 2008/0312570 A1 | * | 12/2008 | Dunagan ............... | A61F 13/046 602/3 |

(Continued)

OTHER PUBLICATIONS

Kim et al., Case Study: Hybrid model for the customized wrist orthosis using 3D printing, Journal of Mechanical Science and Technology, vol. 29 (12), pp. 5151-5156, Jul. 22, 2015.

*Primary Examiner* — Ramesh Patel
(74) *Attorney, Agent, or Firm* — Knobbe Martens Olson & Bear LLP (57) ABSTRACT

A computer-implemented method for modeling an orthopedic cast, including scanning an injured limb to extract raw body data; determining, from the extracted raw body data, a target portion data of the injured limb, the determined data representing a fine cast surface for the orthopedic cast; patterning the fine cast surface to form a ventilation structure and a blank area thereon; forming an opening gap on the blank area for assembling and disassembling the orthopedic cast; and offsetting the cast surface in parallel to thicken the orthopedic cast.

21 Claims, 8 Drawing Sheets

(56) References Cited

U.S. PATENT DOCUMENTS

| | | | |
|---|---|---|---|
| 2010/0138193 A1* | 6/2010 | Summit | G06F 17/50 703/1 |
| 2010/0292963 A1* | 11/2010 | Schroeder | A61F 2/30 703/1 |
| 2014/0208578 A1* | 7/2014 | Linderman | A61F 2/30756 29/592 |
| 2015/0262319 A1* | 9/2015 | Tuttle | G06Q 50/22 705/2 |
| 2015/0328016 A1* | 11/2015 | Summit | A61F 2/5046 703/1 |
| 2016/0339607 A1* | 11/2016 | Munoz | B29C 33/3857 |
| 2017/0216078 A1* | 8/2017 | Rivlin | A61F 5/05866 |

\* cited by examiner

MODELING METHOD FOR ORTHOPEDIC CASTS

TECHNICAL FIELD

The present application relates to a computer-implemented method for modeling an orthopedic cast. More particularly, the present application relates to a method for rapidly modeling a custom-made and 3D-printed orthopedic cast.

BACKGROUND

Bone fractures occur in the general population due to trauma or bone diseases. Plaster or fiberglass casts have been employed for the treatment of most bone fracture patients. Traditional orthopedic casts or orthoses are produced by a body-based contacting model. The bottom mold for the cast is generated from surface shapes of injury limbs and filled up with plasters. Thermoplastic material, PE (Polyethylene) or CPP (copolymer polypropylene), is pasted on the mold and removed after it is cooled down. Bone fracture patients wear plaster splints after the surgery followed by orthoses for further recovery. Those casts may cause several skin diseases and a potential bone and joint injury due to their heavy structure and poor ventilation. Moreover, patients suffer mechanical pressures during the mold manufacture, and multi-reproduction of physical molds is unfeasible.

3D printing technology is a rapid growing manufacture technique for producing complex physical model using 3D digital model. Recently, the 3D printing technology has been extensively applied to surgical practices and medical training. The rapid manufacture of the physical model from medical images provides a technical means that results in minimal invasion in medical planning and treatment. Custom made rehabilitation tools produced using 3D printing technique has been deployed in the new development of orthoses.

Some novel concepts have been proposed as potential substitutes for plaster cast manufactured by the 3D printing technology. The mesh-like structure forms an artistic surface pattern of the model by changing its webby density, providing more solid fracture region with less material in healthy areas.

Another development is a model similar to Cortex but embedded with an ultrasound device for promoting the therapeutic process. Those new designs are fabricated using the 3D printing technique and environment friendly material. The cast geometries are generated from 3D scan models that are patient specific and are capable of offering wearing comfort and fashionable appearance. The mesh-like structure of the model presents excellent ventilation and significantly light weight. However, the mesh-like structure has less strength in supporting the injured limbs. Low intensity mechanical impact may break the webby beam. In addition, the webby shape is most likely to cause crack and fatigue due to the slender connecting bar.

A hybrid model for custom-fit wrist orthoses combines the webby frame with the shell cover to enhance the structural strength of the cast and to keep the ventilation of the cast. The design process mainly includes a process of modeling an inner frame and an outer cover via a CAD system. This approach may increase the stiffness of the model and prevent the model structure from breakage. However, an experienced CAD engineer is required for creating appropriate engineering structure.

Despite the technical advance and economic potential, 3D printing technologies have not become a primary means in fabrication of the orthopedic cast. Significant technical expertise is required for designing the cast, which is costly and timeconsuming. In order to perform a CAD process, the scanned data of subject limbs must be converted into a specific CAD file with geometric modifications. An experienced CAD engineer is required for creating the model and converting the model CAD file to an STL (Standard Template Library) file for 3D printing.

Clinical demands for developing a cast with good ventilation, light weight, and automatic design process and less requirements of expertise, have gotten more and more attention. The medical applications of the 3D printing are increasing due to its manufacture speed and cost effectiveness. The growing 3D printing technologies make it possible to fabricate a complex geometric model in orthopedic casts and significantly reduce the manufacturing time and cost.

SUMMARY

One of the objectives of the application is to develop a rapid modeling technique for custom made orthopedic cast and to overcome the weakness of traditional alternatives, such as weight and ventilation. The proposed modeling method would require less expertise and more automatic than the conventional approaches do.

In an aspect of the application, a computer implemented method for modeling an orthopedic cast is proposed. The method may comprise: scanning an injured limb to extract raw body data; determining, from the extracted raw body data, target portion data of the injured limb, wherein the determined data may represent a fine cast surface for the orthopedic cast; patterning the fine cast surface to form flare edges, a ventilation structure and a blank area thereon; forming an opening gap on the blank area for assembling and disassembling the orthopedic cast; and offsetting the cast surface in parallel to thicken the orthopedic cast.

According to an embodiment of the present application, the method may include stretching points on surface areas near opening ends of the fine cast surface to create flare edges at the opening ends.

The cast surface may be offset by a specific distance to form two parallel cast surfaces without connection on the opening ends. The two parallel cast surfaces maybe linked at the opening ends by connecting edge nodes on one cast surface of the two surfaces with corresponding edge nodes on the other cast surface of the two surfaces.

In one embodiment of the application, the centerline maybe bounded on, for example, the Voronoi diagram of the orthopedic cast and may be composed of points centered the maximal inscribed sphere. The centerline maybe a spline line and may comprise tangent vectors varied along the spline line. The clipping plane maybe defined by a normal vector, which averages a couple of successive tangent vectors from an endpoint of the centerline.

In one embodiment of the application, the method may further comprise applying different extending coefficients on the closest distance between the centerline and the points on the surface areas near the opening ends to stretch the opening ends to create flare edges at the opening ends.

In one embodiment of the application, the cast surface may have a polyline tube shape. The step of patterning the fine cast surface as mentioned in the above may comprise cutting the cast surface along the longitudinal direction of the surface to form a plurality of polyline loops; determining a reference vector for each of the polyline loops to create a bundle of vector lines for locating centers of the ventilation holes along a circumferential direction; determining the blank area in accordance with angles between the reference vector and a start vector line and a symmetric end vector line of the created vector lines; and forming an opening gap on the determined blank area of the cast surface.

As an example, the method may further comprise determining the centers of the ventilation holes in an area other than the blank area of the cast surface; and forming the ventilation holes on the cast surface based on the centers. To this end, the method may further comprise determining a centerline of the cast surface along a longitudinal direction thereof, wherein the centerline may be geometrically defined as a shortest path to connect two endpoints of the orthopedic cast; and removing end portions of the surface, which may be outside of clipping planes, wherein the clipping planes may be normal to the centerline.

In one embodiment of the application, the method may further comprise averaging the tangent vectors along the centerline, wherein the average of the tangent vectors may be employed as a normal line of the cutting planes; integrating all micro segments composing of the centerline to obtain a total length of the centerline; subtracting two marginal lengths from the total length to define an effective length of the centerline; and cutting, within effective length, the cast surface along the longitudinal direction of the surface to form a plurality of surface segments with polyline loops. The cut surface segments may have the same extension length in the longitudinal direction.

According to an embodiment of the application, the centers of the ventilation holes may be located on the polyline loop with the closest distance to the bundle of vector lines. The ventilation holes may be formed by modeling a plurality of spheres with same diameter based on the centers, and removing portions of the cast surface intersecting with the spheres to form the ventilation holes. The opening gap may be formed by creating a path of the opening gap along the reference points and two end points on the flare edges; modeling a tube along the path, wherein the tube may be centered with the path; and removing portions of the cast surface intersecting with the tube to form the opening gap.

In another aspect of the present application, a system for modeling an orthopedic cast from raw body data of an injured limb is proposed. The system may comprise: a memory that may store executable instructions; a processor electrically coupled to the memory that may execute the executable instructions to perform operations of the system. The executable instructions may be configured to: digitize the raw body data and transfer the same as specific type of file; determine, from the extracted raw body data, target portion data of the injured limb, wherein the determined data may represent a fine cast surface for the orthopedic cast; pattern the fine cast surface to form flare edges, a ventilation structure and a blank area thereon; form an opening gap on the blank area for assembling and disassembling the orthopedic cast; and offset the cast surface in parallel to thicken the orthopedic cast.

In a further aspect of the present application, an orthopedic cast modeled from raw body data of an injured limb is proposed. The orthopedic cast may include a cast surface with a tube like shape; flare edges at opening ends of the cast surface; and a surface pattern formed on the cast surface and including a ventilation area and a blank area. A plurality of ventilation holes may be formed on the ventilation area and an opening gap may be formed on the blank area.

According to an embodiment of the application, the ventilation area may comprise a plurality of ventilation holes. In addition, the blank area may comprise an opening gap for assembling and disassembling the cast.

With the modeling method of the present disclosure, less expertise will be required and more automatic will be achieved.

BRIEF DESCRIPTION OF THE DRAWINGS

Exemplary non-limiting embodiments of the present application are described below with reference to the attached drawings. The drawings are illustrative and generally not made according to an exact scale. The same or similar elements on different figures are referenced with the same reference numbers.

DETAILED DESCRIPTION

Reference will now be made in detail to exemplary embodiments, examples of which are illustrated in the accompanying drawings. When appropriate, the same reference numbers are used throughout the drawings to refer to the same or like parts.

Figure 1:
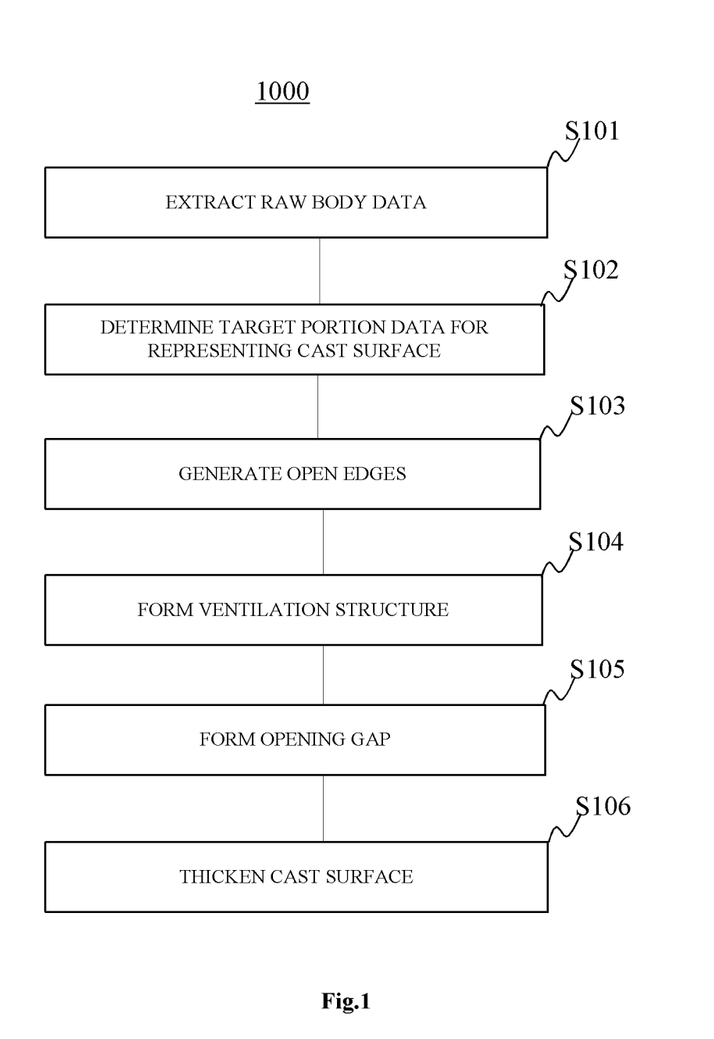
FIG. 1 is a flow diagram showing a process forming a model of an injured limb according to an embodiment of the present application.
Figure 2:
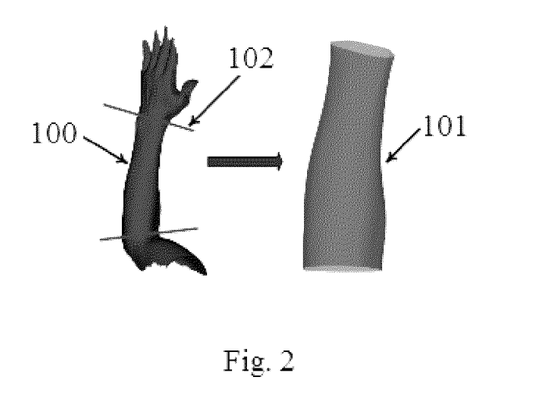
FIG. 2 schematically shows a model built by scanned data of a limb and a raw cast surface cut from the model according to an embodiment of the present application.

FIG. 1 exemplarily illustrates a process 1000 for modeling the cast according to an embodiment of the present application. As shown in FIG. 1, at step S101, an injured limb is scanned, for example, by a scanner, to extract raw body date of the injured limb and then an initial cast surface model may be generated from clipping the raw body data. FIG. 2 schematically shows a model 100 built by scanned data of a limb and a raw cast surface 101 cut from the data according to an embodiment of the present application.

The scanned data of an injured limb may be obtained by, for example, a photometric scanner, Artec Eva and Artec Space Spider (Luxembourg). Patients should be placed in an appropriate position for obtaining the adequate data for reconstructing an image of the injured limb. For example, the surface geometry of limb may be digitized and transferred as a polygonal STL (Standard Template Library) file with over a plurality of points and triangle elements (for example, 200,000 points and 400,000 triangle elements). The number of the points and the elements may vary widely from one anatomic site to another. The initial cast surface model may be generated from clipping the raw body data as shown in FIG. 1.

At step S102, the target portion data for a fine cast surface is determined by clipping the raw body data. The determined data represents a fine cast surface for the orthopedic cast. The cast surface has tube like flare openings at the opening ends, which are formed by stretching points on surface areas near opening ends of the fine cast surface. In this step, a computation of centerline L is proposed to create a fine cast model with a visually perpendicular end plane. After the centerline L is determined, the end portions of the cast surface, which are outside of clipping planes normal to the centerline, will be removed. The clipping location may be determined by orthopedic technicians in accordance with the injury site. It should be noticed that the clipping plane 102 may not be visually perpendicular to the cast surface 101.

Computing centerline L of the raw cast surface 101 is used not only for creating desired edges of the fine cast model 103, but also for subsequent modeling steps. The centerline computation and fine edge clipping process may be implemented as follows.

a) There are many mathematical descriptions of the centerline which is an intuitive central path. The centerline L may be geometrically defined as the shortest path to connect two endpoints of a tube like cast. It should be noted that the centerline L may be bounded on, for example, the Voronoi diagram of the cast and may be composed of points centered the maximal inscribed sphere. In the present embodiment, the centerline L may be calculated by the conventional technical means, such as the Vascular Modeling Toolkit (VMTK, Orobixsrl).

b) Once the centerline L is determined, it may be used to define reference planes to perform a fine clipping. The centerline L may be a spline line and the tangent vectors may vary along the spline line. The clipping plane may be defined by a normal vector, which averages a couple of successive tangent vectors from an endpoint of the centerline L. In this connection, it may use tangent vectors of 5 (as an example) successive points started from an endpoint to calculate the normal vector. However, the number of the successive points is not limited thereto. Two new clipping planes are generated in this step.

c) Two new clipping planes may be applied to the unclipped raw body surface, e.g. body data acquired from 3D scanner, to perform a re-clipping process. The two clipping planes may be located at two endpoints of the centerline and a fine cast surface model 103 may be obtained by re-clipping data.

Figure 4:
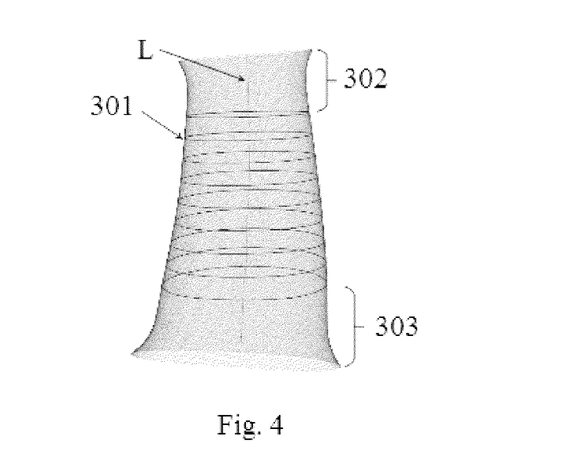
FIG. 4 schematically shows a plurality of polyline loops on the cross section of the cast surface according to an embodiment of the present application.

At step S103, flare openings are generated by stretching points on surface areas near opening ends of the fine cast surface. FIG. 4 schematically shows a perspective view of the cast surface with flare openings according to an embodiment of the present application.

Figure 3:
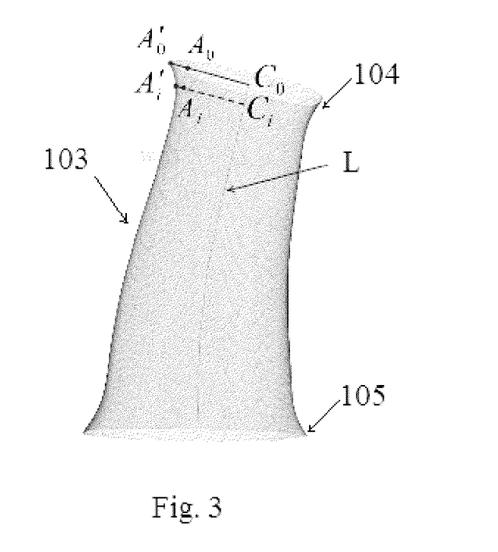
FIG. 3 schematically shows a perspective view of the cast surface with flare openings according to an embodiment of the present application.

The flare opening for tube-like cast geometry may create a funnel-shaped end. Flare edges are required by orthopedists and are modeled in both end sides of the fine cast model to ensure the wearing comfort and safety. The funnel-shaped geometry with round corners may produce a smooth touching surface and thus may prevent injuries from the usual movement of part (such as the wrist) of the injury limbs. Points on the surface areas near the opening edges may be stretched by extending vectors. Referring to FIG. 3, the mathematical form for the extending maybe described as:

$$\vec{A}_i{'} - \vec{C}_i = b_i(\vec{A}_i - \vec{C}_i) \quad (1)$$

Where $C_i$ (i=0, 1, ..., n) are central points on the centerline. $C_i$ is the point with the closest distance to the original surface vertex point $A_i$. $\vec{A}_i{'}$ is the new vertex point stretched from $A_i$. $b_i$ is the extending coefficient with respect to points same layer as $A_i$. Values of coefficient $b_i$ may lineally vary along the centerline.

The maximal extending coefficients may be applied on the opening ends of the tube-like cast. Not all surface points are applied with the extending factor. In this embodiment, surface points with a certain distance (for example, 3~5 mm) to the clipping plane are applied with the extending coefficient. There is no exact standard to determine the values of the coefficients depending on the original geometry. For example, the maximal coefficient used in this embodiment may be 1.15, but the present application is not limited thereto. The funnel-shaped opening ends are more or less intuitive and different values of the maximal coefficient with orthopedic feasibility are acceptable. Flare shapes 104 and 105 may be generated in both sides of the cast 103 in this step.

The process now turns to step S104, in which the fine cast surface is patterned to form a ventilation area and a blank area. FIG. 4 shows a plurality of polyline loops 301 on the cross section of the cast surface 103 according to an embodiment of the present application. This step is to create surface pattern including the ventilation structure and opening gap for mechanical assembly and adjustment purpose. The ventilation structure may include a plurality of ventilation holes. The ventilation holes may be uniformly distributed in a free surface of the cast.

Figure 5:
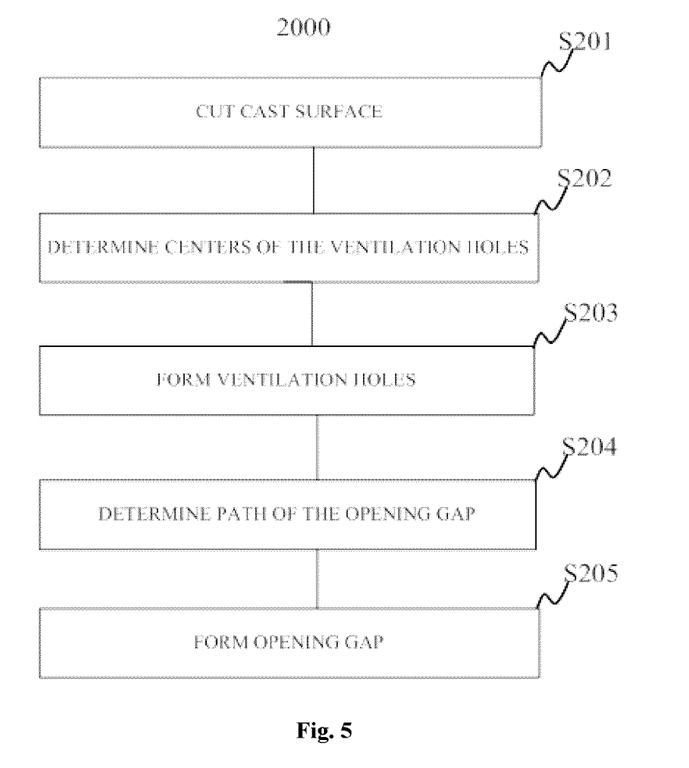
FIG. 5 is a flow diagram showing a process for patterning the cast surface according to an embodiment of the present application.

FIG. 5 shows a process 2000 for patterning the ventilation area and the blank area on the cast surface. In order to pattern the ventilation area and the blank area, it is necessary to determine the position thereof.

The process begins with step S201. In this step, the cast surface is cut along the longitudinal direction of the surface to form a plurality of polyline loops. An algorithm may be developed to perform this step automatically. For example, the algorithm may firstly average the tangent vectors along the centerline, which is a spline line. It then uses the average of the tangents as the normal vector of the cutting planes. For example, the total length of the centerline may be computed by integration of all micro segments that compose of the centerline. The effective length of the centerline may be defined by subtracting two marginal lengths from the total length as illustrated in FIG. 4. The marginal lengths on both opening ends of the cast 103 may be specified by medical engineers in terms of the corresponding standard or experiences. The effective centerline L', which removes two marginal segments 302 and 303 from the centerline L, may be divided by equal distance segments, and then the points in-between segments may be extracted. The cutting planes may be created at each of the points in-between segments and applied on slicing the casting surface to give the polyline loops 301.

Then the process 2000 turns into step S202, in which a reference vector for each of the polyline loops is determined to create a bundle of vector lines for locating centers of the ventilation holes along a circumferential direction. In this step, a user specified point on the cast surface and a mapping point of the user specified point on the centerline is selected.

Figure 6:
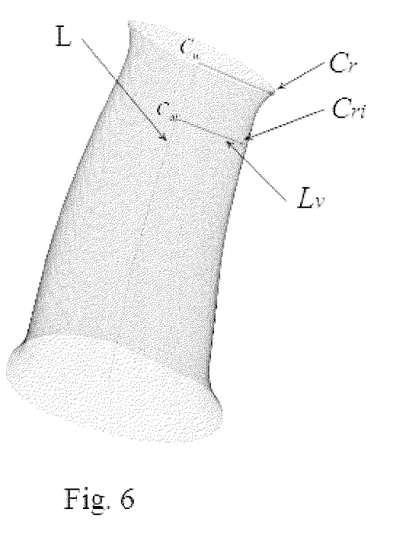
FIG. 6 schematically shows user specified points and a reference point on the cast surface according to an embodiment of the present application.

FIG. 6 shows a user specified point and a reference point on the cast surface according to an embodiment of the present application. Ventilation holes may be uniformly distributed on the free surface of cast in case the stress concentration and weak structure. However, a blank area on the cast surface should be reserved for creating an opening gap running through the cast surface for the consideration of the further mechanical assembly design. That is to say, there is no hole drilling in this area. As shown in FIG. 6, the orthopedic engineer may select a point calling user-specified-point $C_r$ as a marker for creating blank area. The mapping point $C_u$ on the centerline L with the closest distance to the user specified point $C_r$ is selected and a vector line $L_l$ starting from mapping point $C_u$ to user specified point $C_r$ is created. The vector line L1 may be used as a reference line which is formed by extending a line from the mapping point to the user specified point. Then a reference point located on each of the polyline loops is defined. $C_{ai}$ (i=1, 2 ..., n) is a point on the centerline L and located at a cutting plane for generating corresponding polyline loop 301 (FIG. 3). The polyline loops 301 may be generated from the intersection between a cutting plane and cast surface 103. An alpha point $C_{ri}$ may be defined as the reference point located at the polyline loop 301 and served as the starting point to position the centers of holes along this loop. To determine the alpha point, a vector line $L_v$ may be created to pass through $C_{ai}$ and parallel with the vector line passing through $C_u$. that is to say, the reference vector is formed by a line extending from the defined reference point $C_{ri}$ and in parallel to the reference line. The alpha point $C_{ri}$ may be selected from the polyline loop $C_{ri}$ 301 with the closest distance to the vector line $L_l$. Each cutting plane or each polyline loop may have a vector line to be a reference vector as shown in FIG. 6.

Figure 7:
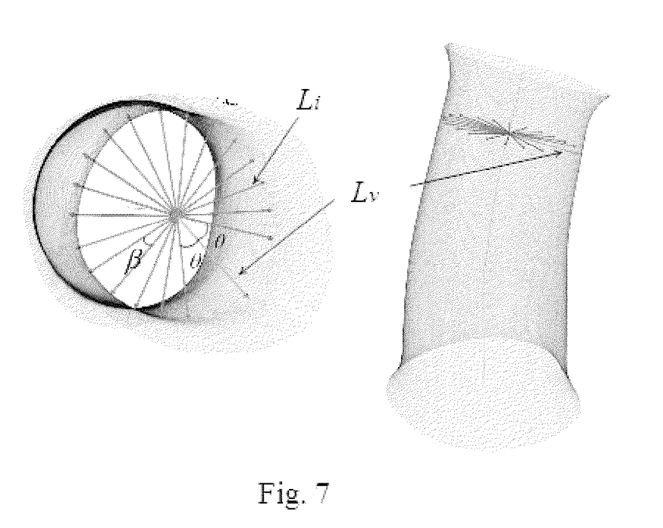
FIG. 7 schematically shows a bundle of vector lines for locating centers of holes according to an embodiment of the present application.

Each reference vector $L_v$ may be used to create a bundle of vector lines $L_i$ for further locating the centers of holes. In terms of technical needs, the number of holes for each slice may be pre-defined. As shown in FIG. 7, in order to reserve a blank area as mentioned above, an angle formed by two vectors, i.e. reference vector and start vector line, may be defined. The value of angle can be θ. In addition, a symmetric end vector line corresponding to the reference vector $L_v$ may also be defined with same orientation angle θ between those two vectors. A circular pattern may be applied to create a bundle of vector lines $L_i$ from the start vector line to the end vector line. The number of vector lines $L_i$ is equal to the required number of holes of each slice. Equal angle β between two adjacent vector lines can be calculated as follows:

$$\beta = \frac{(360 - 2 \cdot \theta)}{m - 1} \quad (2)$$

Where β is the angle between two adjacent vectors and m is the number of holes for each slice. The centers of holes are located at the polyline loop 301 with the closest distance to the vector lines $L_i$. Each vector line $L_i$ determines one hole center.

Once the centers of the ventilation holes are determined, a plurality of spheres with same diameter will be modeled based on the centers. At step S203, the ventilation holes are formed by removing portions of the cast surface intersecting with the spheres.

Figure 8:
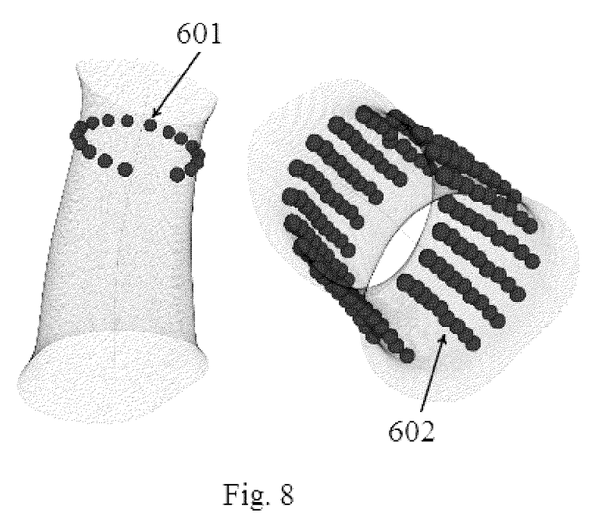
FIG. 8 schematically shows a perspective view of the cast surface with a plurality of micro spheres formed thereon according to an embodiment of the present application.
Figure 9:
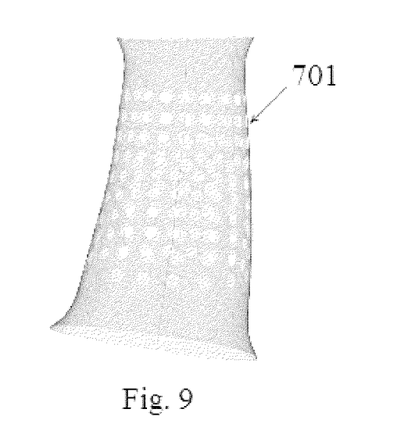
FIG. 9 schematically shows a plurality of holes formed on the cast surface according to an embodiment of the present application.

FIG. 8 shows a perspective view of the cast surface with a plurality of micro spheres formed thereon according to an embodiment of the present application. FIG. 9 shows a plurality of holes formed on the cast surface according to an embodiment of the present application. The detail process for creating the ventilation holes is described as below.

After the centers of holes are selected, a plurality of micro spheres 601 with those centers may be modeled as shown in FIG. 8. Those spheres 601 may have the same diameter, the value of which may be determined based on technical needs. For example, 2 or 3 mm of the diameter may be suggested for upper or lower limbs. However, this is only an example and the diameter of the sphere is not limited thereto. Values may vary on special cases depending on the clinical application. The ventilation holes may be created via geometrically Boolean operation between three-dimensional spheres and the free surface of cast. In particular, this operation subtracts elements inside the sphere 601 from the cast surface 103. As shown in FIG. 9, it then develops a cast surface with uniformly distributed ventilation holes 701. The bigger size of the holes, the lighter weight of the structure will be built. However, the increasing size of the holes suggests that a relatively weak structure is developed due to less solid areas keeping in the structure. Engineering assessment of strength such as the finite element analysis is recommended for validation.

At step S204, the blank area is determined in accordance with angles between the reference vector and a start vector line and a symmetric end vector line of the created vector lines. Generally, the angles are same as each other. After the blank area is determined, a path of the opening gap is created along the reference points and two end points on the flare edges.

Once the ventilation area and the blank area are determined, an opening gap will be formed on the blank area for assembling and disassembling the orthopedic cast.

Figure 12:
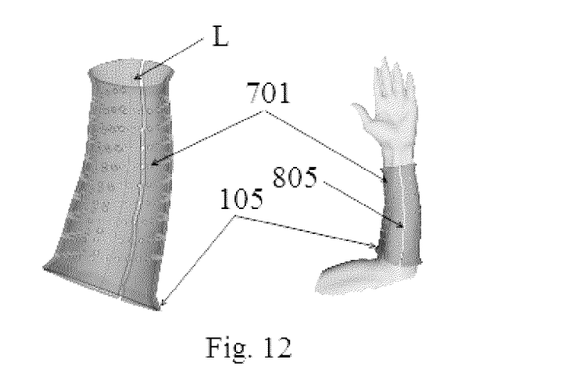
FIG. 12 schematically shows the modeled cast including a centerline, ventilation holes, an opening gap and a flare according to an embodiment of the present application.

FIG. 12 shows a process for forming an opening gap on the cast surface according to an embodiment of the present application. The opening gap is used for assembling and disassembling the cast, and makes the cast adjustable during the treatment of limb injuries. The path of the opening gap may not be a straight line or an intersection line given by a flat plane and the cast surface due to the free curving surface of the cast. Geometric varieties of cast surface make it difficult to simply create the path via extracting intersection line between a flat plane and the cast surface. For example, a geodesics-based approach may be proposed to model a curve as the path of gap. It should be noted that other proper approach under the teaching of the present application can also be used.

The previous steps have created a marker specified to a user on the cast surface. Based on the marker point $C_r$, the array of alpha points $C_{ri}$ may be selected in previous steps as illustrated in FIG. 6. Those points may be added into a control point list. It should be noted that more control points 801 maybe added into the list to ensure that those control points 801 can run through the cast surface 103 along the longitudinal direction. The available control points 801 have two end points 802 and 803 that may be employed as two reference points to locate the two end points on two opening flare edge. Those two end points 802 and 803 have the closest distances to two reference points, respectively. The two end points 802 and 803 will be added into the control point set, i.e., the control point list, to generate a new point set, which will be used to create the profile of an opening gap 805. The geodesics, for example Dijkstra geodesics, can be calculated based on the adjacent control points. Those geodesics may compose of an initial path of the opening gap 805. The initial path will be a zigzag like line that would not have engineering rationality due to high risk on developing crack and fatigue and poor wearing comfort.

Creating a smoothing curve as the path for opening gap 805 is developed in this embodiment. More points located at geodesics will be added into the control point set. The control point set multiplies the points for modeling an accurate and rational path line. A spline line passing through all points in the control point set is built and run through the cast surface 103. The spline line may be defined as the path of the opening gap 805.

At step S205, a tube 806 will be modeled for creating the opening gap 805. The opening gap is formed by removing portions of the cast surface intersecting with the tube. In this step, a circle may be created at one end point of the spline line and sweep along the path to generate the tube 806. The spline line is then served as the centerline of the tube 806. A small size of the tube will develop a small gap which would better enclose the injury limbs. The smaller size of the tube 806, the better cast structure will be modeled. For the consideration of the manufacturing feasibility, e.g. accuracy of 3D printing, the diameter may be set as around, for example, 2 mm. But the diameter of the tube is not limited thereto. A parametric tube may be created for adjustments of the gap space. Once the tube 806 is built, the opening gap 805 will be developed by performing Boolean subtraction between the tube and cast surface as displayed in FIG. 10. That is to say, the opening gap is formed by removing portions of the cast surface intersecting with the tube.

Figure 11:
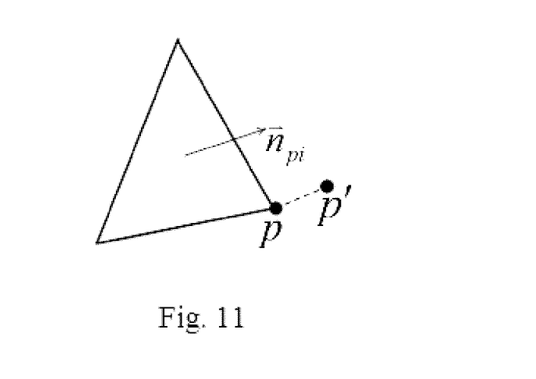
FIG. 11 schematically shows a normal vector of a patch for offsetting a surface vertex according to an embodiment of the present application.

At step S105, the cast surface is offset in parallel so as to thicken the orthopedic cast. FIG. 11 shows a normal vector of a patch for offsetting a surface vertex so as to thicken the cast surface. The thickness of the cast may be built by offsetting the cast surface 103. The cast surface 103 may be composed of a large number of elements with triangle shape. Each of the elements has its normal vector calculated from the cross product of vectors along any two sides of the element. The normal vector pointing to outside cast surface may be considered as the reference direction for offsetting. The offsetting process can be mathematically ruled as:

$$\vec{p}\,' = \vec{p} + t \cdot \vec{n}_{pi} \quad (3)$$

Where $\vec{p}$ is an original vertex of an element; $\vec{p}\,'$ is the offset vertex. $\vec{n}_{pi}$ is the normalized direction vector of the element and t is the thickness. Due to the curve shape of the cast surface with concave shape in some regions, a relatively great thickness may result in wrapping element shapes on the cross section, where sides of two or more elements intersect. A small thickness (e.g. 1 mm) is suggested in each step of offsetting to avoid geometric error. Offsetting elements with a small thickness is able to technically smooth the surface and further reduce the occurrence of wrapping elements. The accumulation of thicknesses can generate the resulting thickness as required by users.

Figure 10:
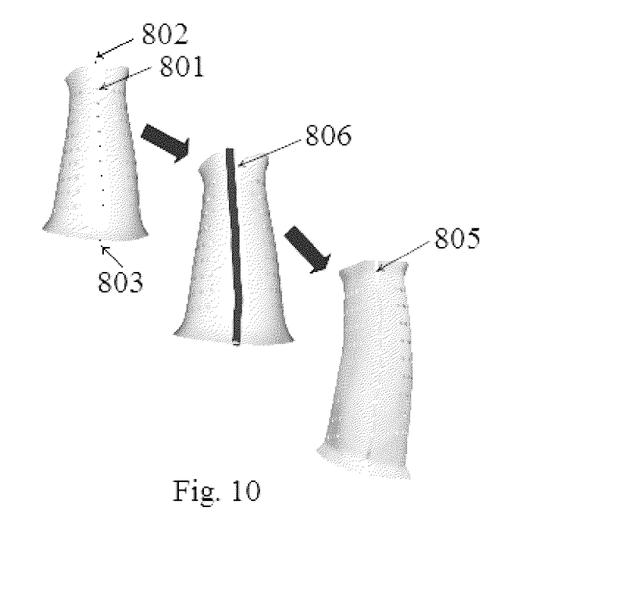
FIG. 10 schematically shows a process for forming an opening gap on the cast surface according to an embodiment of the present application.

FIG. 12 shows the modeled cast 1001 including centerline L, ventilation holes 701, opening gap 805 and flares 104 and 105 according to an embodiment of the present application. As shown in FIG. 10, the offsetting process may generate two parallel cast surfaces without connection on opening ends. In order to create an enclosed cast model, i.e. solid-like model, nodes on opening ends, on both parallel surfaces, should be linked together at the opening ends by connecting an edge node and corresponding offsetting node. Those new lines plus two opening edges and thus the corresponding offsetting edges create two surfaces located at each ends of the cast. An enclosed cast model may include the original and offsetting surfaces plus two end surfaces. The volumic cast model may be developed from the enclosed model and transformed as STL format for 3D printing.

The above steps and related algorithms may be developed by, for example, Visualization Toolkit (VTK, Kitware) and integrated into an intelligent designing system. The cast geometry is built from scanned data making an orthosis custom made.

Figure 13:
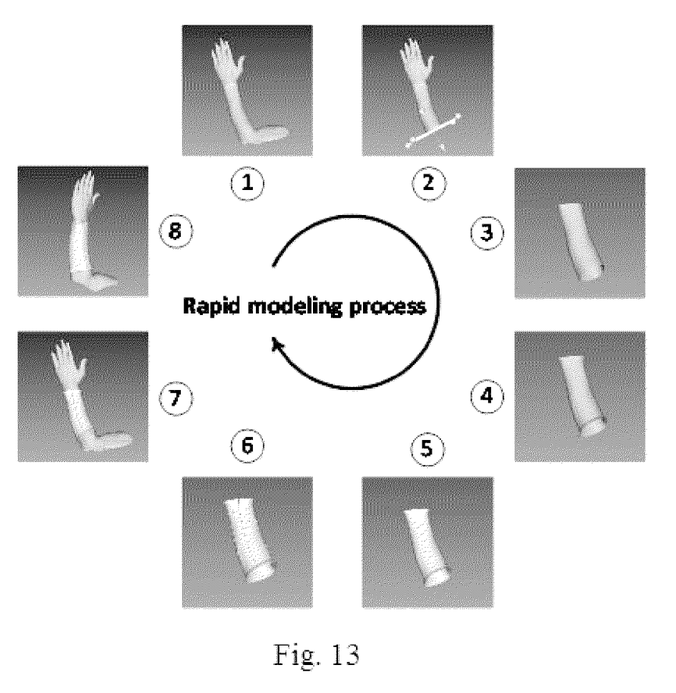
FIG. 13 schematically shows a cast designing process for an arm orthosis according to an embodiment of the present application.

FIG. 13 shows a cast designing process for an arm orthosis according to an embodiment of the present application. The scanned model may include enormous numbers of elements that are rapidly designed by specific algorithms developed in this project. The entire designing process is automatic and a few specific training is required, while experienced CAD designers are necessary for developing conventional orthosis. The proposed model can be adjusted to accommodate swelling from injury limbs quickly by means of the opening gap.

As will be appreciated by one skilled in the art, the present application may be embodied as a system, a method or a computer program product. Accordingly, the present application may take the form of an entirely hardware embodiment and hardware aspects that may all generally be referred to herein as a "unit", "circuit," "module" or "system." Much of the inventive functionality and many of the inventive principles when implemented, are best supported with or integrated circuits (ICs), such as a digital signal processor and software therefore or application specific ICs. It is expected that one of ordinary skill, notwithstanding possibly significant effort and many design choices motivated by, for example, available time, current technology, and economic considerations, when guided by the concepts and principles disclosed herein will be readily capable of generating ICs with minimal experimentation. Therefore, in the interest of brevity and minimization of any risk of obscuring the principles and concepts according to the present application, further discussion of such software and ICs, if any, will be limited to the essentials with respect to the principles and concepts used by the preferred embodiments.

Figure 14:
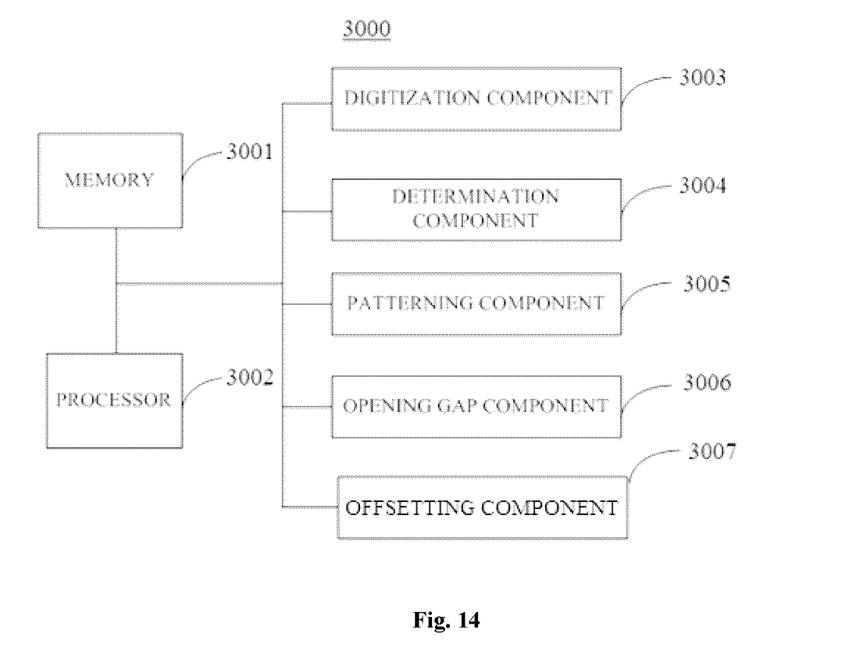
FIG. 14 schematically shows a system for modeling an orthopedic cast from raw body data of an injured limb according to an embodiment of the present application.

In addition, the present application may take the form of an entirely software embodiment (including firmware, resident software, microcode, etc.) or an embodiment combining software. For example, the system may comprise a memory that stores executable components and a processor, electrically coupled to the memory to execute the executable components to perform operations of the system, as discussed in reference to FIGS. 1-14. FIG. 14 illustrates a system 3000 for modeling an orthopedic cast from raw body data of an injured limb, comprising: a memory 3001 that stores executable components and a processor 3002 electrically coupled to the memory that execute the executable components to perform operations of the system, wherein the executable components may comprise: a digitization component 3003 for digitizing the raw body data and transfer the same as specific type of file; a determination component 3004 for determining, from the extracted raw body data, target portion data of the injured limb, wherein the determined data represents a fine cast surface for the orthopedic cast; a patterning component 3005 for patterning the fine cast surface to form a blank area thereon; an opening gap component 3006 for forming an opening gap on the blank area for assembling and disassembling the orthopedic cast; and an offsetting gap component 3007 for offsetting the cast surface in parallel to thicken the orthopedic cast. In one embodiment, the opening gap component 3005 is further configured to stretch points on surface areas near opening ends of the fine cast surface to create flare edges at the opening ends. In a further embodiment, the opening gap component 3005 is further configured to pattern the fine cast surface to form a ventilation structure having a plurality of ventilation holes. The detailed description for the options for these components are the same as discussed in reference to the above discussed method 1000 and thus the entity of literal descriptions thereof is incorporated herein by reference.

Although the preferred examples of the present application have been described, those skilled in the art can make variations or modifications to these examples upon knowing the basic inventive concept. The appended claims are intended to be considered as comprising the preferred examples and all the variations or modifications fell into the scope of the present application.

What is claimed is:

1. A computer-implemented method for modeling an orthopedic cast, comprising:
   scanning an injured limb to extract raw body data;
   determining, from the extracted raw body data, target portion data of the injured limb, the determined target portion data representing a fine cast surface for the orthopedic cast;
   patterning the fine cast surface to form a blank area thereon;
   forming an opening gap on the blank area for assembling and disassembling the orthopedic cast; and
   offsetting the fine cast surface in parallel to thicken the orthopedic cast.

2. The method of claim 1, further comprising:
   stretching points on surface areas near opening ends of the fine cast surface to create flare edges at the opening ends.

3. The method of claim 1, further comprising:
   patterning the fine cast surface to form a ventilation structure having a plurality of ventilation holes.

4. The method of claim 2, wherein the offsetting further comprises:
   offsetting the fine cast surface to form two parallel cast surfaces without connection at the opening ends.

5. The method of claim 4, further comprising:
   linking the two parallel cast surfaces at the opening ends by connecting edge nodes on one of the two parallel cast surfaces with corresponding edge nodes on the other one of the two parallel cast surfaces.

6. The method of claim 3, wherein the fine cast surface has a longitudinal direction, and the method further comprises:
   determining a centerline of the fine cast surface along the longitudinal direction, wherein the centerline is geometrically defined as a shortest path to connect two endpoints of the orthopedic cast; and
   removing end portions of the surface, the end portions being outside of clipping planes and the clipping planes being normal to the centerline.

7. The method of claim 6, wherein the centerline is bounded on the Voronoi diagram of the orthopedic cast and is composed of points centered on the maximal inscribed sphere.

8. The method of claim 6, wherein the centerline is a spline line and comprises tangent vectors varied along the spline line.

9. The method of claim 8, wherein the clipping plane is defined by a normal vector, which averages a couple of successive tangent vectors from an endpoint of the centerline.

10. The method of claim 2, further comprising
    stretching the opening ends to create flare edges at the opening ends by applying different extending coefficients on a closest distance between the centerline and points on the surface areas near the opening ends.

11. The method of claim 8, wherein the fine cast surface is shaped with a polyline tube shape, and wherein the patterning comprises:
    cutting the fine cast surface along a longitudinal direction of the surface to form a plurality of polyline loops;
    determining a reference vector for each of the polyline loops to create a bundle of vector lines for locating centers of the ventilation holes along a circumferential direction of the orthopedic cast;
    determining the blank area in accordance with angles between the reference vector and a start vector line and a symmetric end vector line of the created vector lines; and
    generating the opening gap on the determined blank area of the cast surface.

12. The method of claim 11, wherein the patterning further comprises:
    determining centers of the ventilation holes in an area other than the blank area of the cast surface; and
    generating the ventilation holes on the cast surface based on the centers.

13. The method of claim 11, wherein the cutting further comprises:
    averaging the tangent vectors along the centerline resulting in an average, the average being employed as a normal line of the cutting planes;
    integrating all micro segments composing of the centerline to obtain a total length of the centerline;
    subtracting two marginal lengths from the total length to define an effective length of the centerline; and
    cutting, within the effective length, the cast surface along the longitudinal direction of the surface to form a plurality of surface segments with polyline loops,
    the plurality of surface segments having an identical extension length in the longitudinal direction.

14. The method of claim 11, wherein the reference vector is determined by:
    selecting a user specified point on the cast surface;
    selecting a mapping point of the user specified point on the centerline; and
    defining a reference point located on each of the polyline loops, wherein the reference point is selected from the polyline loops with the closest distance to a reference line from the mapping point to the user specified point;
    wherein the reference vector is formed by a line extending from the defined reference point and in parallel to the reference line.

15. The method of claim 12, wherein the centers of the ventilation holes are located on each of the polyline loops with a closest distance to the bundle of vector lines.

16. The method of claim 15, wherein the ventilation holes are formed by:
   modeling a plurality of spheres with identical diameter based on the centers; and
   removing portions of the cast surface intersecting with the spheres to form the ventilation holes.

17. The method of claim 14, wherein the opening gap is formed by:
   creating a path of the opening gap along the reference points and two end points on the flare edges;
   modeling a tube along the path, the tube being centered with the path; and
   removing portions of the cast surface intersecting with the tube to form the opening gap.

18. The method of claim 4, further comprising:
   creating an enclosed cast model by linking nodes on the opening ends on both parallel surfaces.

19. A system for modeling an orthopedic cast from raw body data of an injured limb, comprising:
   a memory storing executable instructions;
   a processor electrically coupled to the memory executing the executable instructions to perform operations of the system, wherein the executable instructions are configured to:
   digitize the raw body data and transfer the same as specific type of file;
   determine, from the digitized raw body data, target portion data of the injured limb, the determined target portion data representing a fine cast surface for the orthopedic cast;
   pattern the fine cast surface to form a blank area thereon;
   form an opening gap on the blank area for assembling and disassembling the orthopedic cast; and
   offset the cast surface in parallel to thicken the orthopedic cast.

20. The system of claim 19, wherein the executable instructions are configured to stretch points on surface areas near opening ends of the fine cast surface to create flare edges at the opening ends.

21. The system of claim 19, wherein the executable instructions are configured to pattern the fine cast surface to form a ventilation structure having a plurality of ventilation holes.

* * * * *